(12) United States Patent
Tamura et al.

(10) Patent No.: US 8,957,233 B2
(45) Date of Patent: Feb. 17, 2015

(54) METHOD FOR PRODUCING OPTICALLY ACTIVE 1,2-BIS(DIALKYLPHOSPHINO)BENZENE DERIVATIVE

(75) Inventors: Ken Tamura, Tokyo (JP); Masashi Sugiya, Tokyo (JP); Tsuneo Imamoto, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 111 days.

(21) Appl. No.: 13/808,692

(22) PCT Filed: Jul. 3, 2011

(86) PCT No.: PCT/JP2011/065233
§ 371 (c)(1),
(2), (4) Date: Mar. 4, 2013

(87) PCT Pub. No.: WO2012/005200
PCT Pub. Date: Jan. 12, 2012

(65) Prior Publication Data
US 2013/0172597 A1    Jul. 4, 2013

(30) Foreign Application Priority Data
Jul. 8, 2010   (JP) ................... 2010-155399

(51) Int. Cl.
*C07F 9/28*      (2006.01)
*C07F 9/54*      (2006.01)
*C07B 53/00*     (2006.01)
*C07C 67/303*    (2006.01)
*C07C 231/12*    (2006.01)
*C07C 231/18*    (2006.01)
*C07D 207/337*   (2006.01)
*C07D 307/54*    (2006.01)
*C07F 9/50*      (2006.01)
*C07F 15/00*     (2006.01)

(52) U.S. Cl.
CPC ............... *C07F 9/5449* (2013.01); *C07B 53/00* (2013.01); *C07C 67/303* (2013.01); *C07C 231/12* (2013.01); *C07C 231/18* (2013.01); *C07D 207/337* (2013.01); *C07D 307/54* (2013.01); *C07F 9/5022* (2013.01); *C07F 9/5027* (2013.01); *C07F 15/0073* (2013.01); *C07B 2200/07* (2013.01)
USPC .............................................. 556/21; 556/19

(58) Field of Classification Search
CPC ....... C07B 53/00; C07C 227/32; C07F 9/5009
USPC .................................................. 556/19, 21
See application file for complete search history.

(56) References Cited

U.S. PATENT DOCUMENTS 8,198,471 B2 * 6/2012 Tamura et al. ............... 556/21
2010/0234626 A1   9/2010 Tamura et al.

FOREIGN PATENT DOCUMENTS

JP    2000-319288 A    11/2000
JP    2010-208993 A     9/2010

OTHER PUBLICATIONS

Yamamoto, Yoshikazu et al., "Facile Synthesis of Highly Congested 1,2-Diphosphinobenzenes from Bis(phosphine) boronium Salts", Organic Letters, 2006, vol. 8, No. 26, p. 6103-6106, cited in specification and ISR.
Tamura, Ken et al., "Enantiopure 1,2-Bis(tert-butylmethylphosphino)benzene as a Highly Efficient Ligand in Rhodium-Catalyzed Asymmetric Hydrogenation", Organic Letters, 2010, vol. 12, No. 19, p. 4400-4403, cited in ISR.
International Search Report of PCT/JP2011/065233, mailing date of Sep. 27, 2011.

* cited by examiner

*Primary Examiner* — Sudhakar Katakam
*Assistant Examiner* — Pancham Bakshi
(74) *Attorney, Agent, or Firm* — Westerman, Hattori, Daniels & Adrian, LLP

(57) ABSTRACT

An industrially advantageous method for producing an optically active 1,2-bis(dialkylphosphino)benzene derivative of the present invention is provided. The method is characterized in that a phosphine-borane compound represented by the following general formula (1) is subjected to a deboronation reaction, followed by lithiation, then the reaction product is subjected to reaction with an alkyldihalogenophosphine represented by $R^a PX'_2$, and thereafter the reaction product is subjected to reaction with a Grignard reagent represented by $R^b MgX''$ to produce an optically active 1,2-bis(dialkylphosphino)benzene derivative (A). $R^1$ and $R^2$ respectively represent an alkyl group having 1 to 8 carbon atoms, and the number of carbon atoms is different between $R^1$ and $R^2$. $R^a$ is either $R^1$ or $R^2$ and $R^b$ is the other of $R^1$ and $R^2$. X, X', and X" each represent a halogen atom.

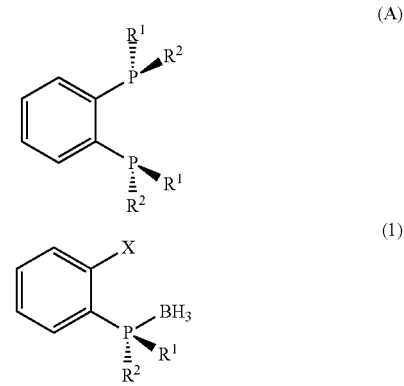

2 Claims, No Drawings

METHOD FOR PRODUCING OPTICALLY ACTIVE 1,2-BIS(DIALKYLPHOSPHINO)BENZENE DERIVATIVE

TECHNICAL FIELD

The present invention relates to a method for producing an optically active 1,2-bis(dialkylphosphino)benzene derivative.

BACKGROUND ART

An optically active phosphine ligand having a chiral center on a phosphorous atom plays an important role in a catalytically asymmetric synthesis reaction using a transition metal complex. A 1,2-bis(dialkylphosphino)benzene derivative has been suggested as an optically active phosphine ligand having a chiral center on a phosphorous atom, for example, in PTL 1. A transition metal complex having this benzene derivative as a ligand is a compound having excellent property as a catalyst for asymmetric synthesis. A method for producing the above mentioned benzene derivative by using 1,2-bis(phosphino)benzene as a stating material is described in PTL 1.

Also, a method for producing an optically active 1,2-bis(dialkylphosphino)benzene derivative is described in NPL 1. In above method, chromium 1,2-difluorobenzenetricarbonyl and borhium bis(ialkylphosphine) salt are used as a starting material.

CITATION LIST

Patent Literature

[PTL 1] JP-A-2000-319288

Non-Patent Literature

[NPL 1] ORGANIC LETTERS, 2006, Vol. 8, No. 26, pp. 6103-6106

SUMMARY OF INVENTION

Technical Problem

However, all starting materials used in the processes described in PTL 1 and NPL 1 are expensive. Those methods are not industrially advantageous from the point of view of economy. Therefore, an object of the present invention is to provide an industrially advantageous method for producing an optically active 1,2-bis(dialkylphosphino)benzene derivative.

Solution to Problem

The present invention accomplished the object by providing a method for producing an optically active 1,2-bis(dialkylphosphino)benzene derivative represented by the following general formula (A), the method characterized in that a phosphine-borane compound represented by the following general formula (1) is subjected to a deboronation reaction, followed by lithiation, then the reaction product is subjected to reaction with an alkyldihalogenophosphine represented by $R^a PX'_2$ (where, $R^a$ is either $R^1$ or $R^2$ defined in the above general formula (A), and X' represents a halogen atom) and thereafter the reaction product is subjected to reaction with a Grignard reagent represented by the general formula $R^b MgX''$ (where, $R^b$ is ether $R^1$ or $R^2$ as defined in the general formula (A), provided that $R^a$ and $R^b$ are not the same, and X'' represents a halogen atom) to produce an optically active 1,2-bis(dialkylphosphino)benzene derivative.

[Chem. 1]

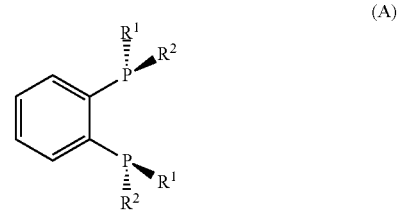

(A)

(Where: $R^1$ and $R^2$ respectively represent an alkyl group having 1 to 8 carbon atoms, and the number of carbon atoms is different between $R^1$ and $R^2$)

[Chem. 2]

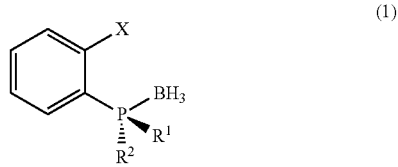

(1)

(Where: $R^1$ and $R^2$ have the same meaning as defined in the above general formula (A), and X represents a halogen atom.)

Also, the present invention provides a method for asymmetric hydrogenation using a transition metal complex having the optically active 1,2-bis(dialkylphosphino)benzene derivative produced by the above-described method as a ligand, as a catalyst.

Advantageous Effects of Invention

The present invention allows the industrially advantageous production of an optically active 1,2-bis(dialkylphosphino)benzene derivative to be realized without using high cost compounds as a starting material. In addition, the production method of the present invention allows an introduction of an alkylphosphino group of the benzene derivative to be made easy even though its size is bulky. Also, an asymmetric hydrogenation reaction can be carried out by using the transition metal complex having the benzene derivative obtained by the production method of the present invention as a ligand, as a catalyst, so as to realize high optical purity and chemical yield.

DESCRIPTION OF EMBODIMENTS

Hereinafter, there will be described the present invention in detail based on a preferred embodiment of the present invention.

The objective material of the production method of the present invention is an optically active 1,2-bis(dialkylphosphino)benzene derivative represented by the above-mentioned general formula (A). In the general formula (A), $R^1$ and $R^2$ respectively represent an alkyl group having 1 to 8 carbon atoms, and the number of carbon atoms is different between $R^1$ and $R^2$. When the number of carbon atoms of $R^1$ is larger than that of $R^2$, the benzene derivative represented by the general formula (A) is an (R,R) isomer. Reversely, when the number of carbon atoms of $R^2$ is larger than that of $R^1$, the benzene derivative represented by the general formula (A) is an (S,S) isomer.

Examples of an alkyl group having 1 to 8 carbon atoms represented by $R^1$ and $R^2$ include an acyclic alkyl group and an alicyclic alkyl group.

The acyclic alkyl group may be a linear alkyl group or a branched alkyl group. Examples of the linear alkyl group include an alkyl group having 1 to 8 carbon atoms, specifically including a methyl group, an ethyl group, a n-propyl group, a n-butyl group, a n-pentyl group, a n-hexyl group, a n-heptyl group, and a n-octyl group. Examples of the branched alkyl group include an alkyl group having 3 to 8 carbon atoms, specifically including an isopropyl group, an isobutyl group, a sec-butyl group, a tert-butyl group, an isoheptyl group, an isohexyl group, and a 1,1,3,3-tetramethylbutyl group. Examples of an alicyclic alkyl group include an alicyclic alkyl group having 3 to 8 carbon atoms, specifically including a cyclopentyl group, a cyclohexyl group and the like. In addition, these alkyl groups may also be substituted with one or more monovalent substituent (for example, a halogen atom such as fluorine, chlorine, bromine, iodine and the like).

It needs that the difference between the number of carbon atoms of $R^1$ and $R^2$ is at least 1. In the general formula (A), it is preferable that the group having a larger number of carbon atoms between $R^1$ and $R^2$ be a bulky substituent having a steric hindrance. In this respect, as the alkyl group having a larger number of carbon atoms between $R^1$ and $R^2$, a secondary alkyl group is preferable to a primary alkyl group, and a tertiary alkyl group is more preferable to a secondary alkyl group. Also, a preferred alkyl group is an alicyclic alkyl group. A tert-butyl group is exemplified as a preferred alkyl group.

Herein, when the benzene derivative represented by the general formula (A) is used as a ligand of metal complex for an asymmetric synthesis catalyst, a highly asymmetric space is formed. Upon considering this fact, it is preferred that there be a great difference between the steric hindrance of $R^1$ and $R^2$. That is to say, it is preferred that one of $R^1$ and $R^2$ be a bulky substituent having a steric hindrance, namely, a maximal group, whereas the other is a minimal group. Thus, the larger the difference between the number of carbon atoms of $R^1$ and $R^2$ is the better. Specifically, the difference between the number of carbon atoms of $R^1$ and $R^2$ is preferably 2 or more, particularly preferably 3 or more, and further particularly preferably 4 or more. Upon considering that the one having a smaller number of carbon atoms between $R^1$ and $R^2$ is a minimal group, an acyclic alkyl group is preferable to an alicyclic alkyl group when the alicyclic alkyl group and the acyclic alkyl group have the same number of carbon atoms as each other. Also, among acyclic alkyl groups having the same number of carbon atoms, a linear alkyl group is more preferable to a branched alkyl group. Finally, it can be said that the most preferred group as an alkyl group having a smaller number of carbon atoms between $R^1$ and $R^2$ is a methyl group. However, in general, a group that can be used as a group having a smaller number of carbon atoms is relatively determined based on the relationship with the other group having a larger number of carbon atoms. An example of a preferred combination of $R^1$ and $R^2$ is a combination of $R^1$=a tert-butyl group and $R^2$=a methyl group; and a combination of $R^1$=a methyl group and $R^2$=a tert-butyl group.

Meanwhile, the two $R^1$ of the general formula (A) may be identical to or different from each other, and preferably identical to each other. The same rule will be applied to the two $R^2$ of the general formula (A). For the two $R^1$ and two $R^2$, as well either of the two —$PR^1R^2$ groups in the general formula (A), the number of carbon atoms of $R^1$ may be larger than that of $R^2$, and vice versa.

The benzene ring of the benzene derivative represented by the general formula (A) may be substituted with 1 to 4 monovalent substituents. Examples of such a substituent include a methyl group, an ethyl group, a propyl group, a butyl group, a methoxy group, an ethoxy group, a trifluoromethyl group, 1,4-butylene group and the like.

In the production method of the present invention, first, a phosphine-borane compound represented by the general formula (1) is subjected to a deboronation reaction as the first procedure. The deboronation is a reaction represented by the reaction formula 1 below. In the general formula (1), X is a halogen atom such as fluorine, chlorine, bromine, iodine and the like, and a preferred halogen atom is bromine.

(Reaction formula 1)

[Chem. 3]

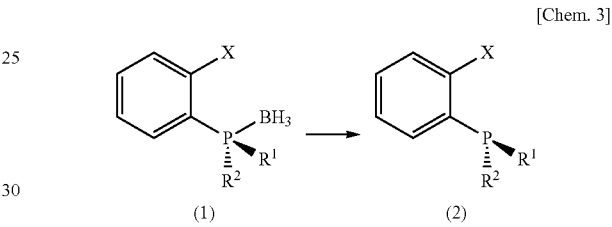

The phosphine-borane compound represented by the general formula (1) used in the production method of the present invention as a starting material can be synthesized according to the reaction formula (i).

Reaction formula (i)

[Chem. 4]

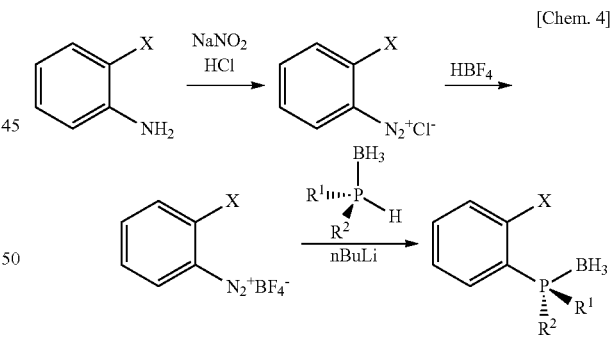

In the reaction formula (i), 2-halogenoaniline is first diazotized to produce diazonium salts. Such 2-halogenoaniline may be a commercially available product. The diazotization reaction can be carried out according to an ordinary method. For example, the reaction is carried out in the presence of sodium nitrite. Such diazonium salts can be isolated in the form of tetrafluoroborate. Subsequently, the obtained diazonium salts are allowed to react with dialkylphosphine-borane.

The dialkylphosphine-borane allowed to react with the diazonium salts can be prepared by a known method such as the method described in JP-A-2001-253889. The dialkylphosphine-borane is deprotonated in an inactive solvent such as tetrahydrofuran. For such deprotonation, butyllithium is used, for example. The deprotonated dialkylphosphine-borane reacts with the above mentioned diazonium salts. This reaction rapidly progresses in an extremely low temperature environment or at room temperature. As a result of this reaction, a phosphine-borane compound represented by the general formula (1) is produced in the reaction system.

In the phosphine-borane compound represented by the general formula (1), an S-diastereomer is used as a dialkylphosphine-borane in a case where the number of carbon atoms of $R^1$ is larger than that of $R^2$ (when the phosphine-borane compound is a R-diastereomer). Contrary to this case, in the phosphine-borane compound represented by the general formula (1), an R-diastereomer is used as a dialkylphosphine-borane in case where the number of carbon atoms of $R^2$ is larger than that of $R^1$ (when the phosphine-borane compound is an S-diastereomer).

Further, when the objective material of the present invention to be obtained is the benzene derivative represented by the general formula (A) of which benzene ring in the general formula (A) has a substituent, the substituent can be easily introduced at the step of 2-halogenoaniline in the reaction formula (i). The introduction of a substituent can be carried out according to an ordinary method.

The deboronation of the phosphine-borane compound represented by the general formula (1), which is the first procedure in the production method of the present invention, can be carried out according to an ordinary known method. The deboronation reaction can be carried out in the presence of a base such as 1,4-diazabicyclo[2.2.2]octane (DABCO), N-methylmorpholine, triethylamine, pyrrolidine, diethylamine and the like, for example, in an organic solvent such as THF, hexane, toluene, dimethoxyethane and the like. A preferred base among the above mentioned bases is DABCO. The amount of the base to be used is preferably from 1 mole to 3 moles, relative to 1 mole of the phosphine-borane represented by the general formula (1). Also, the reaction time is generally from 0.5 hour to 5 hours. And, the reaction temperature is generally from 20 to 110° C.

Next, a lithiation is carried out as the second procedure of the production method of the present invention. The lithiation is represented by the reaction formula 2 below.

(Reaction formula 2)

[Chem. 5]

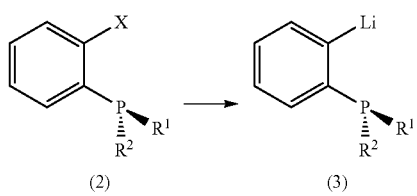

The lithiation can be carried out according to a method known in the related art. For example, it can be carried out using butyl lithium in an organic solvent such as THF, hexane, toluene, dimethoxyethane and the like. The examples of butyl lithium include n-butyl lithium, sec-butyllithium, tert-butyllithium and the like, and preferred butyl lithium is sec-butyl lithium among them. The amount of butyl lithium to be used is preferably from 1.0 mole to 1.5 mole, relative to 1.0 mole of the phosphine-borane compound represented by the general formula (1) used in the first procedure. Also, the reaction time is generally from 0.5 hour to 5 hours. The reaction temperature is generally from −100 to 200° C.

Then, as the third procedure, the reaction product obtained from the second procedure is subjected to reaction with an alkyldihalogenophosphine represented by $R^aPX'_2$ (where, $R^a$ is either $R^1$ or $R^2$ defined in the general formula (A), and X' represents a halogen atom). It is preferred that $R^a$ be a group having a larger number of carbon atoms either $R^1$ or $R^2$. Examples of a halogen atom represented by X include fluorine, chlorine, bromine, iodine and the like, and chlorine is preferred. An alkyldihalogenophosphine represented by $R^aPX'_2$ may be a commercially available product. Also, the alkydihalogenophosphine can be industrially produced at a low price (for example, see JP-A-2002-255983, JP-A-2001-354683, and the like). In case where $R^a$ is $R^1$, the reaction of the third procedure is represented by the reaction formula 3 below.

(Reaction formula 3)

[Chem. 6]

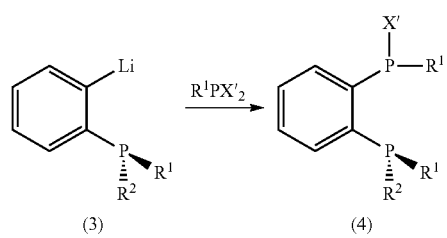

The reaction of the third procedure can be carried out in an organic solvent such as THF, hexane, toluene, dimethoxyethane and the like. The amount of an alkyldihalogenophosphine represented by $R^aPX'_2$ to be used in this procedure is preferably from 1.0 to 2.0 mole, relative to 1 mole of a phosphine-borane compound represented by the general formula (1) used in the first procedure. Also, the reaction time is generally from 0.5 to 24 hours. The reaction temperature is generally from −100 to 20° C.

Subsequently, as the fourth procedure, the reaction product obtained from the third procedure is subjected to reaction with a Grignard reagent represented by $R^bMgX''$ (where, $R^b$ is ether $R^1$ or $R^2$ as defined in formula (A), provided that $R^a$ and $R^b$ are not the same, and X'' represents a halogen atom). Examples of a halogen atom represented by X'' include fluorine, chlorine, bromine, iodine and the like, and chlorine and bromine are preferred. In a case where $R^b$ is $R^2$, the reaction of the fourth procedure is represented by the reaction formula 4 below.

(Reaction formula 4)

[Chem. 7]

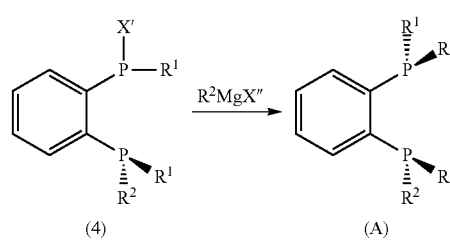

The reaction of the fourth procedure can be carried out according to a ordinary known Grignard reaction. The reaction of the fourth procedure can be carried out in an organic solvent such as THF, hexane, toluene, dimethoxyethane and the like. The amount of a Grignard reagent represented by $R^b MgX''$ to be used in this procedure is preferably from 1.0 to 3.0 mole relative to 1 mole of a phosphine-borane compound represented by the general formula (1) used in the first procedure. Also, the reaction time is generally from 0.5 to 24 hours. The reaction temperature is generally from 0 to 100° C.

Meanwhile, it is preferred that the reactions of the above first to fourth procedures are carried out under inert gas.

An optically active 1,2-bis(dialkylphosphino)benzene derivative represented by the general formula (A), which is the objective material of the present invention, can be obtained by the first to the fourth procedures mentioned above. The benzene derivative which is the objective material of the present invention is either a (R,R) diastereomer or a (S,S) diastereomer. Thus, after the first to the fourth procedures, there is a case where a (R,S) diastereomer or a (S,R) diastereomer, for example, a mixture containing a meso compound may be produced other than the subject material of the present invention. For example, in a case where the objective material is a (R,R) diastereomer, the two $R^1$ are the same alkyl group, and the two $R^2$ are the same alkyl group, a mixture of a (R,R) diastereomer and a meso compound may be produced. Because of this, when either a (R,R) diastereomer or a (S,S) diastereomer, which is the objective material of the present invention, is separated from the mixture, if necessary, by performing a purification step (a), the objective material with high purity can be obtained. This separation step may be performed according to an ordinary purification method, and generally, recrystallization is sufficient to accomplish the separation step. Also, this separation step can be carried out by column chromatography, if necessary. When performing the purification step (a), it is preferred that a further purification step (a') be properly performed by a purification operation such as desolvation, cleansing and the like.

The phosphine-borane compound represented by the above general formula (1), which is used in the production method of the present invention as a starting material, has one $PR^1R^2BH_3$ group, and the compound represented by the above general formula (2), which is obtained by the deboronation of the compound represented by the general formula (1), has one $PR^1R^2$ group. It is difficult to introduce directly further one —$PR^1R^2$ group into X site of these compounds because of the steric hindrance due to the bulky volume of —$PR^1R^2$ group. Therefore, in the present invention, first, either $R^1$ or $R^2$ is introduced into the compound represented by the general formula (2) together with a phosphorous atom, and then, the other one of $R^1$ or $R^2$ is introduced thereinto. By performing this stepwise process, it is possible to easily introduce a —$PR^1R^2$ group to be introduced in spite of its bulky volume.

In addition, in the production method of the present invention, the first to the fourth procedures can be carried out sequentially, and thus there is a merit that the desired optically active 1,2-bis(dialkylphosphino)benzene derivative can be industrially advantageously obtained.

The above optically active 1,2-bis(dialkylphosphino)benzene derivative represented by the general formula (A) obtained by the production method of the present invention can form a complex with a transition metal, as a ligand. Examples of a transition metal capable of forming a complex include rhodium, ruthenium, iridium, palladium, nickel, iron, copper, and the like. A preferred metal is rhodium. As a method for forming a complex from rhodium and the optically active 1,2-bis(dialkylphosphino)benzene derivative represented by the general formula (A), which is used as a ligand, the method described in Experimental Chemistry Course, $4^{th}$ edition (edited by The Chemical Society of Japan, published by Maruzen Co., Ltd., Vol. 18, pp. 327-353) may be applied, for example. Specifically, the optically active 1,2-bis(dialkylphosphino)benzene derivative represented by the general formula (A) is allowed to react with bis(cyclooctane-1,5-diene)rhodium hexafluoroantimonate, bis(cyclooctane-1,5-diene)rhodium tetrafluoroborate and the like, to produce a rhodium complex.

Thus obtained rhodium complex will be specifically exemplified, [Rh((S,S)-(A))(cod)]Cl, [Rh((S,S)-(A))(cod)]Br, [Rh((S,S)-(A))(cod)]I, [Rh((R,R)-(A))(cod)]Cl, [Rh((R,R)-(A))(cod)]Br, [Rh((R,R)-(A))(cod)]I, [Rh((S,S)-(A))(cod)]SbF$_6$, [Rh((S,S)-(A))(cod)]BF$_4$, [Rh((S,S)-(A))(cod)]ClO$_4$, [Rh((S,S)-(A))(cod)]PF$_6$, [Rh((S,S)-(A))(cod)]BPh$_4$, [Rh((R,R)-(A))(cod)]SbF$_6$, [Rh((R,R)-(A))(cod)]BF$_4$, [Rh((R,R)-(A))(cod)]ClO$_4$, [Rh((R,R)-(A))(cod)]PF$_6$, [Rh((R,R)-(A))(cod)]BPh$_4$, [Rh((S,S)-(A))(nbd)]SbF$_6$, [Rh((S,S)-(A))(nbd)]BF$_4$, [Rh((S,S)-(A))(ndb)]ClO$_4$, [Rh((S,S)-(A))(ndb)]PF$_6$, [Rh((S,S)-(A))(ndb)]BPh$_4$, [Rh((R,R)-(A))(nbd)]SbF$_6$, [Rh((R,R)-(A))(nbd)]BF$_4$, [Rh((R,R)-(A))(ndb)]ClO$_4$, [Rh((R,R)-(A))(ndb)]PF$_6$, [Rh((R,R)-(A))(ndb)]BPh$_4$ and the like. Preferred is [Rh((S,S)-(A))(cod)]SbF$_6$, or [Rh((R,R)-(A))(cod)]SbF$_6$ in the present invention. Meanwhile, it is to be noted that the indication (A) in the above rhodium complexes represents the optically active 1,2-bis(dialkylphosphino)benzene derivative represented by the general formula (A), the term "cod" represents 1,5-cyclooctadiene, the term "nbd" represents norbornadiene, and the term "Ph" represents phenyl.

A transition metal complex having the optically active 1,2-bis(dialkylphosphino)benzene derivative represented by the general formula (A) as a ligand (hereinafter, also referred to as a transition metal complex relating to the present invention) is useful catalyst for an asymmetric synthesis. Examples of such asymmetric synthesis include an asymmetric hydrogenation reaction, an asymmetric hydrosylation reaction, an asymmetric Michael addition reaction and the like. Such an asymmetric synthesis reaction can be carried out in the same manner as an ordinary method except for using the transition metal complex relating to the present invention.

The transition metal complex relating to the present invention is particularly suitable for an asymmetric hydrogenation reaction as a catalyst. Examples of compounds used as a substrate in an asymmetric hydrogenation reaction include a compound having a C=C double bond containing a prochiral carbon atom or a C=C double bond. Specific examples of such a compound include α-dehydroamino acid, β-dehydroamino acid, itaconic acid, enamide, β-ketoester, enol ester, α,β unsaturated carbonic acid, β,γ unsaturated carbonic acid, and the like. Preferably, the larger the value of the molar ratio of a substrate to the transition metal complex relating to the present invention (substrate/catalyst), the better without limit, but in practice, it is preferred that the ratio is generally from 100 to 100,000.

EXAMPLES

The present invention will be specifically described in the following examples. However, the examples are provided for illustrative purpose only, and are not intended to limit the scope of the present invention.

Production Example 1

Synthesis of (R)-2-(boranato(tert-butyl)methylphosphino)bromobenzene

In accordance with the reaction formula below, (R)-2-(boranato(tert-butyl)methylphosphino)bromobenzene was synthesized by the following procedures.

[Chem. 8]

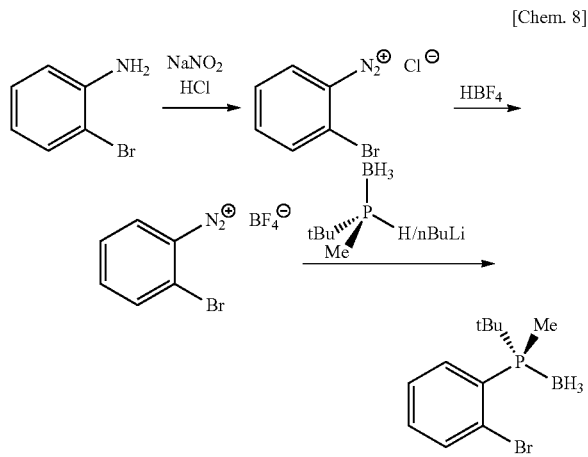

9.5 mL of concentrated hydrochloric acid, 65 mL of pure water, and 6.0 g (35 mmol) of 2-bromoaniline were put into a 200 mL four-necked flask, and they were then dissolved by heating. The obtained solution was cooled to 0° C. Thereafter, an aqueous solution of 2.46 g (35.1 mmol) of sodium nitrite that had previously been dissolved in 7.5 mL of pure water was added dropwise thereto over approximately 10 minutes. The reaction solution that was first in a gruel-like state was converted to a light yellow transparent liquid by stirring for 30 minutes. Subsequently, 12.5 g (59.8 mmol) of a 42 mass % HBF$_4$ aqueous solution was added dropwise thereto over approximately 5 minutes. As a result, light yellow crystals were immediately precipitated. The reaction solution was stirred for 30 minutes, and then the crystals were filtered through a glass filter. The resultant was washed with 30 mL of pure water, and was then washed with a mixed solution of 8 mL of methanol and 32 mL of ether. Thereafter, the resultant was dried under a reduced pressure, so as to obtain 4.5 g of 2-bromobenzenediazonium tetrafluoroborate (yield: 48%).

236 mg (2.00 mmol) of (S)-tert-butylmethylphosphine-borane was put into a well dried 30 mL Schlenk tube, followed by Ar purge. Thereafter, 6 mL of dehydrated THF was added thereto and then dissolved by stirring. The obtained solution was cooled to −78° C., and 1.5 mL (2.4 mmol) of hexane solution of n-BuLi (1.6 mol/L) was slowly added to the solution. The obtained mixture was stirred for 20 minutes, and 650 mg (2.40 mmol) of 2-bromobenzenediazonium tetrafluoroborate was added in small amounts to the reaction solution. The temperature of a dark red-purple transparent solution was increased to room temperature for 2 hours, and the solution was then stirred at room temperature for 2 hours. A saline solution and ethyl acetate were added to the solution to separate the organic layer, and it was then washed with a saline solution. The resultant was dried over MgSO$_4$, and the solvent was then concentrated, followed by purification by silica gel chromatography, so as to obtain 60 mg of (R)-2-(boranato(tert-butyl)methylphosphino)bromobenzene (yield: 11%). The analytical results of the obtained compound are shown below.

(Analytical Results)

$^1$H NMR (500 MHz, CDCl$_3$) δ:

0.20-1.05 (m, 3H), 1.19 (d, J=14.3 Hz, 9H), 1.91 (d, 9.7 Hz, 3H), 7.32 (t, 8.7 Hz, 1H), 7.40 (t, 7.5 Hz, 1H), 7.64 (d, 9.0 Hz, 1H), 8.06 (dd, 12.6, 12.9 Hz, 1H);

$^{31}$P NMR (202 MHz, CDCl$_3$) δ: 38.3.

APCI-MS: m/z 275, 273 (M$^+$+H).

Example 1

Synthesis of (R,R)-1,2-bis(tert-butylmethylphosphino)benzene

In accordance with the reaction formula below, (R,R)-1,2-bis(tert-butylmethylphosphino)benzene was synthesized by the following procedures.

[Chem. 9]

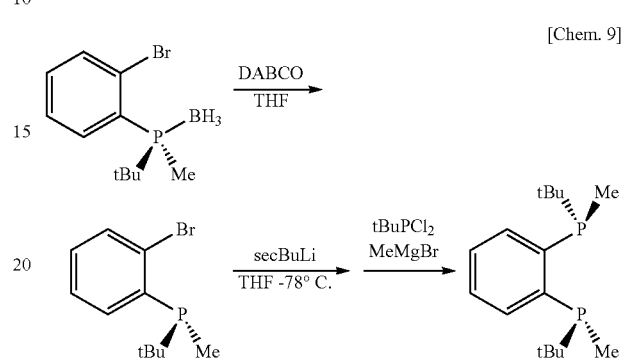

1.365 g (5.00 mmol) of (R)-2-(boranato(tert-butyl)methylphosphino)bromobenzene obtained in Production Example 1 and 589 mg (5.25 mmol) of 1,4-diazabicyclo[2.2.2]octane (DABCO) were put into a well dried 50 mL 2-necked flask, followed by Ar purge. Thereafter, 10 mL of dehydrated tetrahydrofuran was added thereto, and then dissolved by stirring. The obtained solution was subjected to reaction at about 70° C. for 2 hours under mild reflux. Then, the solution was cooled to −78° C., and 5.10 mL of hexane solution of sec-butyllithium (1.03 mol/L) was slowly added to the solution with syringe. Thirty minutes later, 3 mL of THF solution of tert-butyldichlorophosphine 875 mg (5.5 mmol) was added thereto at once, and then the temperature of the solution was increased to room temperature (20° C.) for 1 hour and was stirred for further 1 hour. Thereafter, the temperature of the solution was cooled to 0° C., and 12.5 mL of THF solution of methylmagnesiumbromide (0.96 mol/L) was added thereto with syringe. The temperature of the solution was increased to room temperature, and was stirred for further 1 hour. Subsequently, most of solvent was concentrated, and 25 mL of degassed hexane and 10 mL of 15 mass % NH$_4$Cl aqueous solution were added thereto. After separating the hexane layer, the resultant was washed with saturated saline solution and was dried over Na$_2$SO$_4$. Thereafter, the solvent was concentrated, followed by adding a degassed methanol to the remaining oily product. The resulting crystals were filtered, followed by washing with small amounts of cooled methanol, and were dried under reduced pressure to obtain 539 mg of (R,R)-1,2-bis(tert-butylmethylphosphino)benzene in the form of colorless crystals (yield: 38%). The analytical results of the obtained compound are shown below.

(Analytical Results)

$^1$H NMR (500 MHz, CDCl$_3$) δ: 0.96

(t, J=6.0 Hz, 18H), 1.23 (t, J=3.2 Hz, 6H), 7.26-7.35 (m, 2H), 7.48-7.50 (m, 2H)

$^{13}$C NMR (125 MHz, CDCl$_3$) δ: 5.69

(t, J=6.0 Hz), 27.24 (t, 8.4 Hz), 30.37 (t, 7.2 Hz), 127.75 (S), 131.47 (S), 144.86 (t, 6.0 Hz)

$^{31}$P NMR (202 MHz, CDCl$_3$) δ: −25.20 (s).

APCI-MS: m/z 283 (M$^+$+H).

HRMS (TOF): Calcd. for C$_{16}$H$_{28}$NaP$_2$: 305.1564, Found: 305.1472

Mp. 125-126° C.

$[\alpha]_D^{24}$: +222.9

(c, 0.535, EtOAc)

Production Example 2

Synthesis of rhodium(1) ((R,R)-1,2-bis(tert-butylmethylphosphino)benzene)(1,5-cyclooctadiene) hexafluoroantimonate In accordance with the reaction formula below, rhodium(1) ((R,R)-1,2-bis(tert-butylmethylphosphino)benzene) (1,5-cyclooctadiene)hexafluoroantimonate was synthesized by the following procedures.

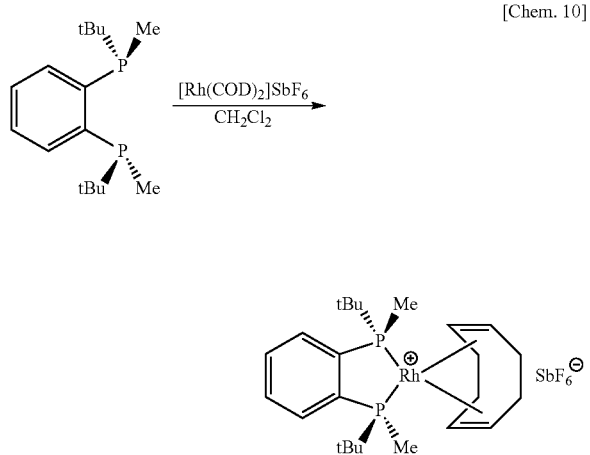

[Chem. 10]

44.8 mg (0.08 mmol) of [Rh(cod)$_2$]SbF$_6$ was put into a well dried 10 mL 2-necked flask, followed by Ar purge. Thereafter, 1 mL of dehydrated dichloromethane was added thereto, and then dissolved by stirring. 24.8 mg (0.088 mmol) of (R,R)-1,2-bis(tert-butylmethylphosphino)benzene obtained in Example 1 and 1 mL of dichloromethane were added dropwise thereto. The color of the solution changed from dark-red to orange. After stirring at room temperature for 30 minutes, the solution was concentrated to 0.5 mL, and 2 mL of diethylether was then added dropwise thereto. The resulting orange-colored crystals were filtered, followed by washing with diethylether, and they were dried under a reduced pressure, so as to obtain 57.6 mg of rhodium(1) ((R,R)-1,2-bis(tert-butylmethylphosphino)benzene) (1,5-cyclooctadiene) hexafluoroantimonate (yield: 98%). The analytical results of the obtained compound are shown below.

(Analytical Results)

$^1$H NMR (500 MHz, CDCl$_3$) δ: 1.05

(d, J=14.s3 Hz, 18H), 1.73 (t, J=8.9 Hz, 6H), 2.20-2.25 (m, 4H), 2.50-2.57 (m, 2H), 2.65-2.69 (m, 2H), 4.89-4.90 (m, 2H), 5.99 (t, J=6.9 Hz, 2H), 7.74 (t, J=2.3 Hz, 4H)

$^{31}$P NMR (202 MHz, CDCl$_3$) δ: 57.59

(d, J=158 Hz)

HRMS (TOF): Calcd. for C$_{24}$H$_{40}$P$_2$Rh: 493.1660, Found: 493.1574

Examples 2-1 to 2-8

Asymmetric Hydrogenation Reaction of α-Dehydroamino Acid

In accordance with the reaction formula below, an asymmetric hydrogenation reaction of α-dehydro aminoacid is performed.

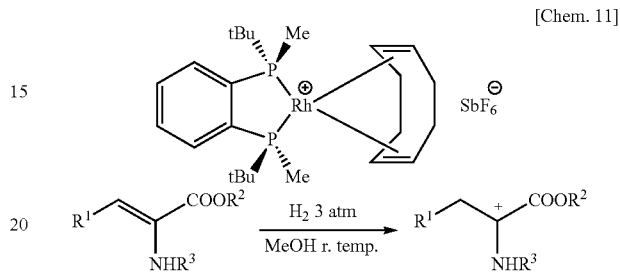

[Chem. 11]

Example 2-1 will be specifically described below. 460 mg (2.10 mmol) of methyl 2-(N-acetylamino)-3-phenyl-2-propenoate which is an α-dehydroamino acid as a substrate and 1.50 mg (2.06×10$^{-3}$ mmol) of rhodium(1) ((R,R)-1,2-bis (tert-butylmethylphosphino)benzene) (1,5-cyclooctadiene) hexafluoroantimonate obtained in Production Example 2 as an asymmetric hydrogenation catalyst were added to a 50 mL glass autoclave. Hydrogen purge was then carried out five times, and 5 mL of dehydrated methanol that had previously been degassed was added thereto. Subsequently, the hydrogen pressure was set to 3 atmospheres, and the reaction was then initiated. The reaction was carried out at room temperature while stirred. Twenty minutes after initiation of the reaction, the consumption of hydrogen in the vessel was stopped, and thus the reaction was assumed to be terminated. The reaction solution was concentrated, and the remaining white crystals were then dissolved in ethyl acetate. The obtained solution was passed through a silica gel column. The obtained eluate was subjected to HPLC analysis. As a result, it was found that (R)-methyl 2-(N-acetylamino)-3-phenylpropanoate was obtained at an enantiomeric excess (ee) of 99.9%. In addition, the compound was analyzed by $^1$H NMR. As a result, the chemical yield was found to be 99% or more. Meanwhile, the following conditions were applied to the HPLC analysis.

(Conditions for HPLC Analysis)

Column Daicel Chiralcel OJ, 1.0 mL/min, hexane:2-propanol=9:1

The retention time of each enantiomer (R) t$_1$=13.3 min., (S) t$_2$=19.3 min.

In Examples 2-2 to 2-8, an asymmetric hydrogenation reaction was carried out in same manner as Example 2-1, using the conditions described in Table 1. Meanwhile, R$^1$ to R$^3$ described in Table 1 correspond to R$^1$ to R$^3$ in the general formula representing the substrate of the reaction formula. Also, in Examples 2-2 to 2-8, the amount of catalyst was the same as Example 2-1 and the amount of substrate changed so as to be the molar ratio of the substrate to relative to catalyst (S/C) described in Table 1.

The conditions for an asymmetric hydrogenation reaction of Examples 2-1 to 2-8 and the obtained result are summarized in Table 1 below.

TABLE 1

| Ex. | $R^1$ | $R^2$ | $R^3$ | Optical purity | Chemical yield | S/C | Reaction time |
| --- | --- | --- | --- | --- | --- | --- | --- |
| 2-1 | Ph | Me | $CH_3CO$ | 99.9% ee | >99% | 1,000 | 20 min. |
| 2-2 | Ph | Me | $CH_3CO$ | 99% ee | >99% | 10,000 | 20 hours |
| 2-3 | Ph | H | $CH_3CO$ | 99.9% ee | >99% | 1,000 | 1 hour |
| 2-4 | $3\text{-}F\text{---}C_6H_4$ | H | $CH_3CO$ | 99.4% ee | >99% | 1,000 | 45 min. |
| 2-5 | H | Me | $CH_3CO$ | 99.7% ee | >99% | 500 | 30 min. |
| 2-6 | $3\text{-MeO-4-AcO }C_6H_3$ | Me | $CH_3CO$ | 99.9% ee | >99% | 500 | 20 min. |
| 2-7 | Furan-2-yl | Me | $PhCH_2OCO$ | 99.1% ee | >99% | 200 | 3 hours |
| 2-8 | Pyrrol-2-yl | Me | $PhCH_2OCO$ | 94% ee | >99% | 200 | 5 hours |

* All hydrides obtained in Examples 2-1 to 2-8 were R-enantiomer.

Examples 3-1 to 3-7

Asymmetric Hydrogenation of β-Dehydroamino Acid

In accordance with the reaction formula below, an asymmetric hydrogenation reaction of β-dehydroamino acid is performed.

[Chem. 12]

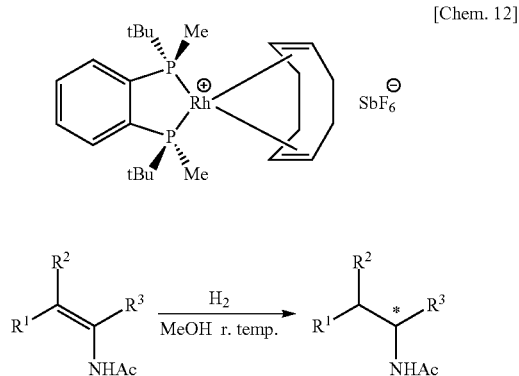

Example 3-1 will be specifically described below. 450.2 mg (2.86 mmol) of (E)-methyl 3-acetamide-2-butenoate which is a β-dehydroamino acid as a substrate and 2.07 mg (2.84×10$^{-3}$ mmol) of rhodium(1) ((R,R)-1,2-bis(tert-butylmethylphosphino)benzene) (1,5-cyclooctadiene)hexafluoroantimonate obtained in Production Example 2 as an asymmetric hydrogenation catalyst were added to a 50 mL glass autoclave. Hydrogen purge was then carried out five times, and 5 mL of dehydrated methanol which had previously been degassed was added thereto. Subsequently, the hydrogen pressure was set to 3 atmospheres, and the reaction was then initiated. The reaction was carried out at room temperature while stirred. Fifty minutes after initiation of the reaction, the consumption of hydrogen in the vessel was stopped, and thus the reaction was assumed to be terminated. The reaction solution was concentrated, and the remaining white crystals were then dissolved in ethyl acetate. The obtained solution was passed through a silica gel column. The obtained eluate was subjected to GC analysis. As a result, it was found that (R)-methyl 3-acetamide butanoate was obtained at an enantiomeric excess (ee) of 99.6%. In addition, the compound was analyzed by $^1$H NMR. As a result, the chemical yield was found to be 99% or more. Meanwhile, the following conditions were applied to the GC analysis.

(Conditions for GC Analysis)

Column Varian Chirasil DEX CB, 135° C.

The retention time of each enantiomer (S) $t_2$=7.6 min., (R) $t_2$=8.1 min.

In Examples 3-2 to 3-7, an asymmetric hydrogenation reaction was carried out in the same manner as Example 3-1, using the conditions described in Table 2.

Meanwhile, $R^1$ to $R^3$ described in Table 2 correspond to $R^1$ to $R^3$ of the general formula representing the substrate of the reaction formula. In Examples 3-5 and 3-6, a mixture of an E-isomer ($R^1$ is H, and $R^2$ is MeOOC) and a Z-isomer ($R^1$ is MeOOC, and $R^2$ is H) (molar ratio 1:1) was used as a substrate. Also, in Examples 3-2 to 3-7, the amount of catalyst was the same as Example 3-1 and the amount of substrate changed so as to be the molar ratio of the substrate relative to catalyst (S/C) described in Table 2. The conditions for an asymmetric hydrogenation reaction of Example 3-1 to 3-7 and the obtained result are summarized in Table 2 below.

TABLE 2

| Example | $R^1$ | $R^2$ | $R^3$ | Optical purity | Chemical yield | S/C | Reaction time |
| --- | --- | --- | --- | --- | --- | --- | --- |
| 3-1 | H | MeOOC | Me | 99.6% ee | >99% | 1,000 | 50 min. |
| 3-2 | H | MeOOC | Me | 99.7% ee | >99% | 200 | 50 min. |
| 3-3 | MeOOC | H | Me | 97.9% ee | >99% | 200 | 45 min. |
| 3-4 | MeOOC | H | Me | 97.6% ee | >99% | 1,000 | 45 min. |
| 3-5 | (E):(Z) = 1:1 | | Me | 98.7% ee | >99% | 1,000 | 50 min. |
| 3-6 | (E):(Z) = 1:1 | | Me | 97.9% ee | 90% | 5,000 | 20 hours |
| 3-7 | MeOOC | H | Ph | 97.2% ee | >99% | 1,000 | 30 min. |

* All hydrides obtained in Examples 3-1 to 3-6 were R-enantiomer, and the hydride obtained in Example 3-7 was S-enantiomer.

Example 4

Asymmetric Hydrogenation Reaction of Dimethyl Itaconate

In accordance with the reaction formula below, an asymmetric hydrogenation reaction of dimethyl itaconate is performed.

[Chem. 13]

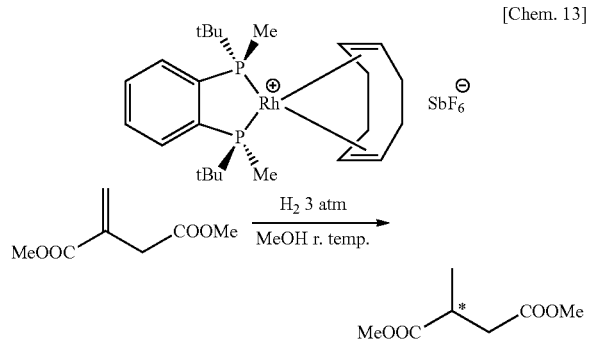

395 mg (2.50 mmol) of dimethyl itaconate as a substrate and 3.64 mg (5.00×10$^{-3}$ mmol) of rhodium(1) ((R,R)-1,2-bis(tert-butylmethylphosphino)benzene) (1,5-cyclooctadiene) hexafluoroantimonate obtained in Production Example 2 as an asymmetric hydrogenation catalyst were put into a 50 mL glass autoclave. Hydrogen purge was then carried out five times, and 5 mL of dehydrated methanol which had previously been degassed was added thereto. Subsequently, the hydrogen pressure was set to 3 atmospheres, and the reaction was then initiated. The reaction was carried out at room temperature while stirred. One hour after initiation of the reaction, the consumption of hydrogen in the vessel was stopped, and thus the reaction was assumed to be termonated. The reaction solution was concentrated, and the remaining white crystals were then dissolved in ethyl acetate. The obtained solution was passed through a silica gel column. The obtained eluate was subjected to HPLC analysis. As a result, it was found that dimethyl (S)-methyl succinate was obtained at an enantiomeric excess (ee) of 97.2%. In addition, the compound was analyzed by $^1$H NMR. As a result, the chemical yield was found to be 99% or more. Meanwhile, the following conditions were applied to the HPLC analysis.
(Conditions for HPLC Analysis)
Column Daicel Chiralcel OD-H, 0.8 mL/min, hexane:2-propanol=98:2
The retention time of each enantiomer (R) t$_1$=7.9 min., (S) t$_2$=12.0 min.

Furthermore, in the above production example and examples, an (R,R) isomer of the benzene derivative represented by the general formula (A) was produced by the production method of the present invention (Example 1), thereafter, a transition metal complex was produced using the (R,R) isomer as a ligand (Production Example 2), and an asymmetric hydrogenation was carried out by using the transition metal complex as a catalyst (Examples 2 to 4). From the above-described production examples and examples, it is clear to a person skilled in the related art that an (S,S) isomer of the benzene derivative represented by the general formula (A) can be produced by the production method of the present invention, and the transition metal complex can be produced by using the (S,S) isomer as a ligand, and also an asymmetric hydrogenation process can be carried out by using the transition metal complex as a catalyst so as to realize high optical purity and chemical yield.

The invention claimed is:

1. A method for preparing an optically active 1,2-bis(dialkylphosphino)benzene derivative represented by the following general formula (A), characterized in that a phosphine-borane compound represented by the following general formula (1) is subjected to deboronation reaction, followed by lithiation, then the reaction product is subjected to reaction with an alkyldihalogenophosphine represented by R$^a$PX'$_2$ (where, R$^a$ is either R$^1$ or R$^2$ defined in formula (A), and X' represents a halogen atom) and thereafter the reaction product is subjected to reaction with a Grignard reagent represented by the general formula R$^b$MgX" (where, R$^b$ is either R$^1$ or R$^2$ as defined in formula (A), provided that R$^a$ and R$^b$ are not the same, and X" represents a halogen atom) to produce an optically active 1,2-bis(dialkylphosphino)benzene derivative

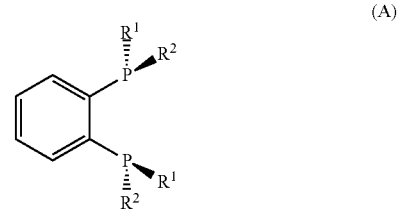

(where R$^1$ and R$^2$ respectively represent an alkyl group having 1 to 8 carbon atoms, and the number of carbon atoms is different between R$^1$ and R$^2$)

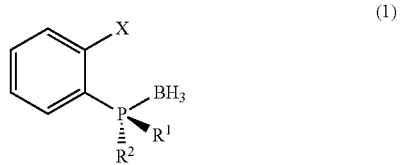

(where R$^1$ and R$^2$ have the same meaning as defined in formula (A), and X represents a halogen atom).

2. A method for asymmetric hydrogenation, comprising:
carrying out the method of claim 1 to prepare the optically active 1,2-bis(dialkylphosphino)benzene derivative represented by the following general formula (A); and
performing asymmetric hydrogenation by using the transition metal complex having optically active 1,2-bis(dialkylphosphino)benzene derivative as ligand, as a catalyst.

* * * * *